(12) United States Patent
Tengshe et al.

(10) Patent No.: US 6,637,883 B1
(45) Date of Patent: Oct. 28, 2003

(54) GAZE TRACKING SYSTEM AND METHOD

(76) Inventors: Vishwas V. Tengshe, B-601 Sanjeev Enclave, 7 Bungalow, JP Road, Versova Andheri (W), Bombay 400 061 (IN); Hemant V. Tengshe, 141-20 85th Rd., Apartment 3F, Briarwood, NY (US) 11435; Venkatesh G. Tengshe, B-601 Sanjeev Enclave, 7 Bungalow, JP Road, Versova Andheri (W), Bombay 400 061 (IN)

( * ) Notice: Subject to any disclaimer, the term of this patent is extended or adjusted under 35 U.S.C. 154(b) by 0 days.

(21) Appl. No.: 10/349,435

(22) Filed: Jan. 23, 2003

(51) Int. Cl.[7] .................................................. A61B 3/14
(52) U.S. Cl. ........................................................ 351/210
(58) Field of Search ................................. 351/209, 210; 382/103; 345/7, 8, 9; 600/426, 417, 429

(56) References Cited

U.S. PATENT DOCUMENTS

| | | | |
|---|---|---|---|
| 4,648,052 A | 3/1987 | Friedman et al. | |
| 4,836,670 A | 6/1989 | Hutchinson | |
| 4,950,069 A | 8/1990 | Hutchinson | |
| 4,973,149 A | 11/1990 | Hutchinson | |
| 5,331,149 A | 7/1994 | Spitzer et al. | |
| 5,345,281 A | 9/1994 | Taboada et al. | |
| 5,367,315 A | 11/1994 | Pan | |
| 5,471,542 A | 11/1995 | Ragland | |
| 5,481,622 A | 1/1996 | Gerhardt et al. | |
| 5,850,211 A | 12/1998 | Tognazzini | |
| 6,006,126 A | * 12/1999 | Cosman | 600/426 |
| 6,215,471 B1 | 4/2001 | DeLuca | |
| 6,373,961 B1 | * 4/2002 | Richardson et al. | 382/103 |
| 6,388,707 B1 | 5/2002 | Suda | |
| 6,394,602 B1 | 5/2002 | Morrison et al. | |
| 2002/0101568 A1 | 8/2002 | Eberl et al. | |
| 2002/0105482 A1 | 8/2002 | Lemelson et al. | |

* cited by examiner

*Primary Examiner*—George Manuel
(74) *Attorney, Agent, or Firm*—Richard C. Litman

(57) ABSTRACT

An eye-tracking system for displaying a video screen pointer at a point of regard of a user's gaze. The system comprises a camera focused on the user's eye; a support connected to the camera for fixing the relative position of the camera to the user's pupil; a computer having a CPU, memory, video display screen, an eye-tracking interface, and computer instructions for: segmenting the digital pixel data of the image of the eye into black and white sections based upon user selectable RGB threshold settings; determining the center of the eye based upon the segmented digital data; mapping the determined center of the eye to a pair of coordinates on the video screen; and displaying a pointer on the video display screen at the point of the regard. The processing performed by the computer includes a fine-tuning capability for positioning the cursor at point on the video screen substantially overlapping the point of regard, and a gaze activated method for selecting computer actions. The system includes additional user mounted sensors for determining the axial position of the camera, thereby compensating for inadvertent eye movement when the point of regard has not changed.

7 Claims, 12 Drawing Sheets

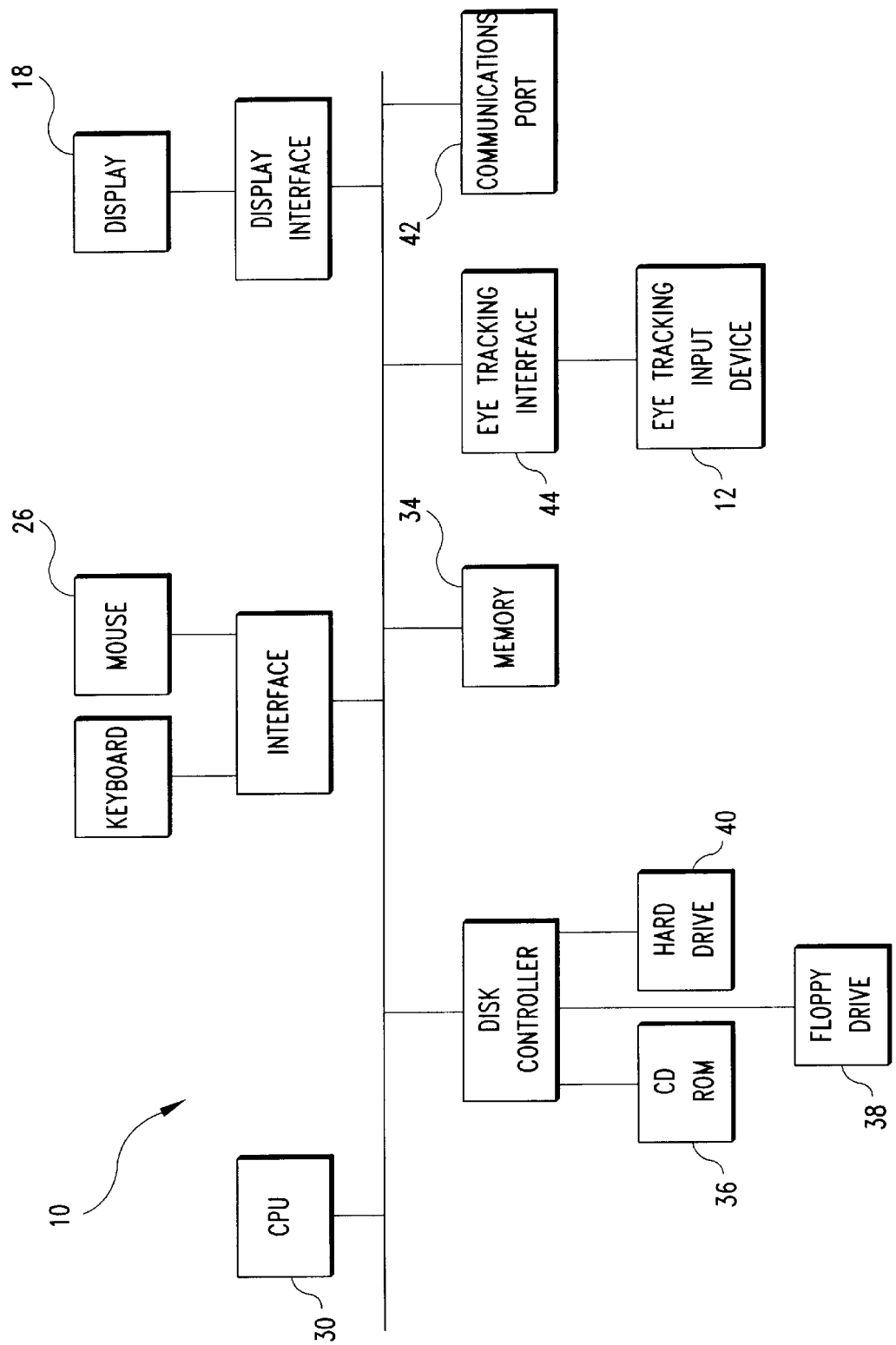

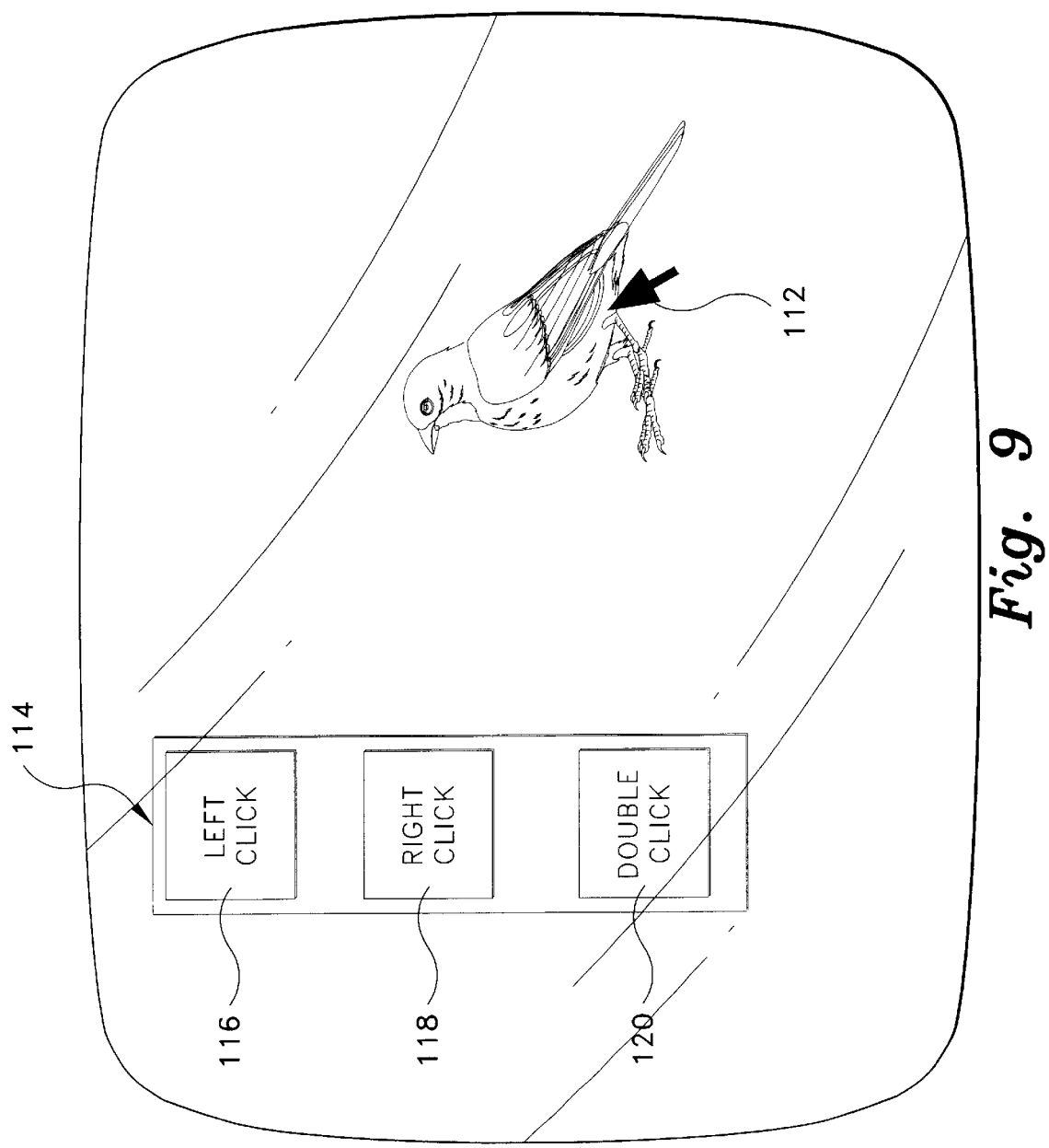

GAZE TRACKING SYSTEM AND METHOD

BACKGROUND OF THE INVENTION

1. Field of the Invention

The present invention relates generally to computer systems and peripherals. More specifically, the present invention is an eye-tracking system and method for determining the direction of a user's gaze, positioning a display pointer at a point of regard, and for controlling a computer by employing the movement of the user's eyes.

2. Description of the Related Art

Eye controlled devices have been used to control the operation of a computer, and more specifically, have used a sensor to track the position of the center of the eye as the eye gazes upon a point of regard, to position a pointer on a video screen.

U.S. Pat. No. 5,345,281, issued to Taboada et al. in 1994 discloses a device for computer cursor positioning by tracking the gaze of the human eye by the analysis of the reflection off the eye of an infrared beam, and requires manual activation of controls. U.S. Pat. No. 5,367,315, issued to Pan in 1994, discloses an eye-controlled device with manual or foot activation. These devices are neither well suited for users requiring a hands-free environment, nor are these devices well suited for those users who are physically challenged.

Another user mounted device is disclosed in U.S. Pat. No. 5,481,622, issued to Gerhardt et al. in 1996, and discloses a helmet mounted camera, video screen, a computer connected to a frame grabber which in turn is connected to the camera, and a computer program for calibrating the position of the user's eye to the video screen and for providing feedback to the user in the form of a cursor on the display screen at a position determined by the gaze of the user. The Gerhardt system determines the center of the user's eye by binary segmentation of the digitized image determined by setting thresholds for the properties of the pixel image. This method of encoding threshold levels for digitized video signals is further disclosed in U.S. Pat. No. 4,648,052, issued to Friedman et al. in 1987, for an eye tracker communication system. Still another head mounted eye sensing unit is disclosed by Eberi, et al. in U.S. patent application Ser. No. 2002/0101568, which includes a signal input unit, a wireless communications unit, and an output unit.

While in some situations a user mounted camera may be seen as an encumbrance, remote mounted tracking devices are ill-suited when the user is actively moving their head or body independent of gazing at a point of regard. U.S. Pat. Nos. 4,836,670; 4,950,069; and 4,973,149 issued to Hutchinson disclose eye mouse devices remote from the user that not only control the movement of a cursor on a computer screen or display by the movement of the user's eyes, but furthermore, the activation or selection is accomplished by the user dwelling, gazing, or staring at a desired activation region for a pre-determined amount of time. Further examples of this type of device are seen in U.S. Pat. No. 5,850,211, issued to Tognazzini in 1998, which discloses a eye track driven scrolling device mounted to the top of a video terminal and U.S. Pat. No. 6,215,471, issued to DeLuca in 2001, which discloses a computer pointer controlled by a camera mounted on a display terminal aimed at the user's face, further disclosing selection of controls by the closure of one or both of the user's eyes.

An attempt to correct this limitation is disclosed by Lemelson et al. in U.S. patent application Publication Ser. No. 2002/0105482 in which a gimbaled sensor system incorporates servo mechanisms mounted on a fixed display terminal to track the user's head and eye movements. Mechanical devices, however, are by themselves a limitation and are not suitable for all applications.

Other eye-tracking devices use an eye sensor focused on the eye of the user to view the image created by the reflected light on the retina to determine the direction of user gaze. Such a device is disclosed in U.S. Pat. No. 6,394,602, issued to Morrison et al. in 2002.

Another point of gaze tracker is U.S. Pat. No. 5,471,542, issued to Ragland in 1995, and discloses a video camera aimed at the user's eye to analyze the digital image formed by the iridal ellipse, the points being on the boundary between the eye's sclera and the iris as represented by different light intensities.

An additional eye tracking system was disclosed in U.S. Pat. No. 5,331,149, issued to Spitzer et al. in 1994, and refers to a system using a photo detector array to detect light reflecting from a user's eye.

Another image pickup apparatus was disclosed in U.S. Pat. No. 6,388,707, issued to Suda in 2001, and refers to a system capable of range finding comprising infrared light sources and charge coupled detectors.

None of the above inventions and patents, taken either singularly or in combination, is seen to describe the instant invention as claimed. Thus a computer-pointing device actuated by eye movement solving the aforementioned problems is desired.

SUMMARY OF THE INVENTION

The invention is an eye-tracking system which determines the point of regard of the user's gaze based upon the position of a user's eye relative to a position on a display screen, comprising a camera for acquiring a video image of the eye; a support for the camera; an eye tracking interface connected to the camera for accepting and converting analog video data from the camera and converting the analog data to digital pixel data; a computer coupled to the interface for processing the digital data from the camera; and specialized computer software which determines the position of the user's gaze depending upon an analysis of the pixel intensity of the digitized image. (The camera, of course, could be using monochrome or color film, or it could be a digital camera.) The computer provides feedback to the user in the form of a pointer positioned on the display screen positioned at the point of the user's gaze and provides the user with the capability to perform computer actions based upon the length of time the user locks his view on the point of regard. The system may include additional sensors mounted proximate to the camera for determining the axial position of the camera, thereby compensating for perceived eye movement when in fact, the point of regard has not changed. The user mounted sensors, eye tracking interface and computer may communicate by wire or by wireless means.

Accordingly, it is a principal object of the invention to provide a system for tracking the movement of a user's eye and correlate its position relative to a specific location on a video screen that includes: a camera focused on the eye of a user, a CPU, a memory, a video screen, an eye tracking interface, a computer readable program code means stored in the memory, and a means for reading the computer readable program code into the memory either from another computer or from a computer useable medium having computer readable program code means embodied thereon.

It is another object of the invention to provide a method for compensating for unintentional movement of the video screen, the camera or both, relative to the user's eye, after calibration of the system.

It is a further object of the invention to provide an eye-tracking computer pointing device that can replace or supplement a conventional handheld computer mouse.

Still another object of the invention is to provide an alternative to a "joy stick" for video game industry.

An additional object of the invention is to provide a virtual keyboard as a replacement for a standard computer keyboard.

It is another object of the invention to provide a usable interface for handicapped persons to control any computer-controlled device having a video screen and a communication port.

It is an object of the invention to provide improved elements and arrangements thereof for the purposes described which is inexpensive, dependable and fully effective in accomplishing its intended purposes.

These and other objects of the present invention will become readily apparent upon further review of the following specification and drawings.

BRIEF DESCRIPTION OF THE DRAWINGS

FIG. 2 is a system block diagram of the present invention according to FIG. 1A.

FIG. 9 is a screen display illustrating the user selection menu according to the present invention.

Similar reference characters denote corresponding features consistently throughout the attached drawings.

DETAILED DESCRIPTION OF THE PREFERRED EMBODIMENTS

The present invention is a system and method for tracking the movement of the eye, placing a pointer on a video screen at the point of regard of the user, placing a menu of selectable user actions and the selection of the aforementioned actions based upon locking the gaze of the eye upon a point of regard for a pre-determined period of time. The invention is capable of embodiment in many forms. The present disclosure is an exemplification of the principles of the invention and does not limit the invention to the illustrated embodiments.

Figure 1A:
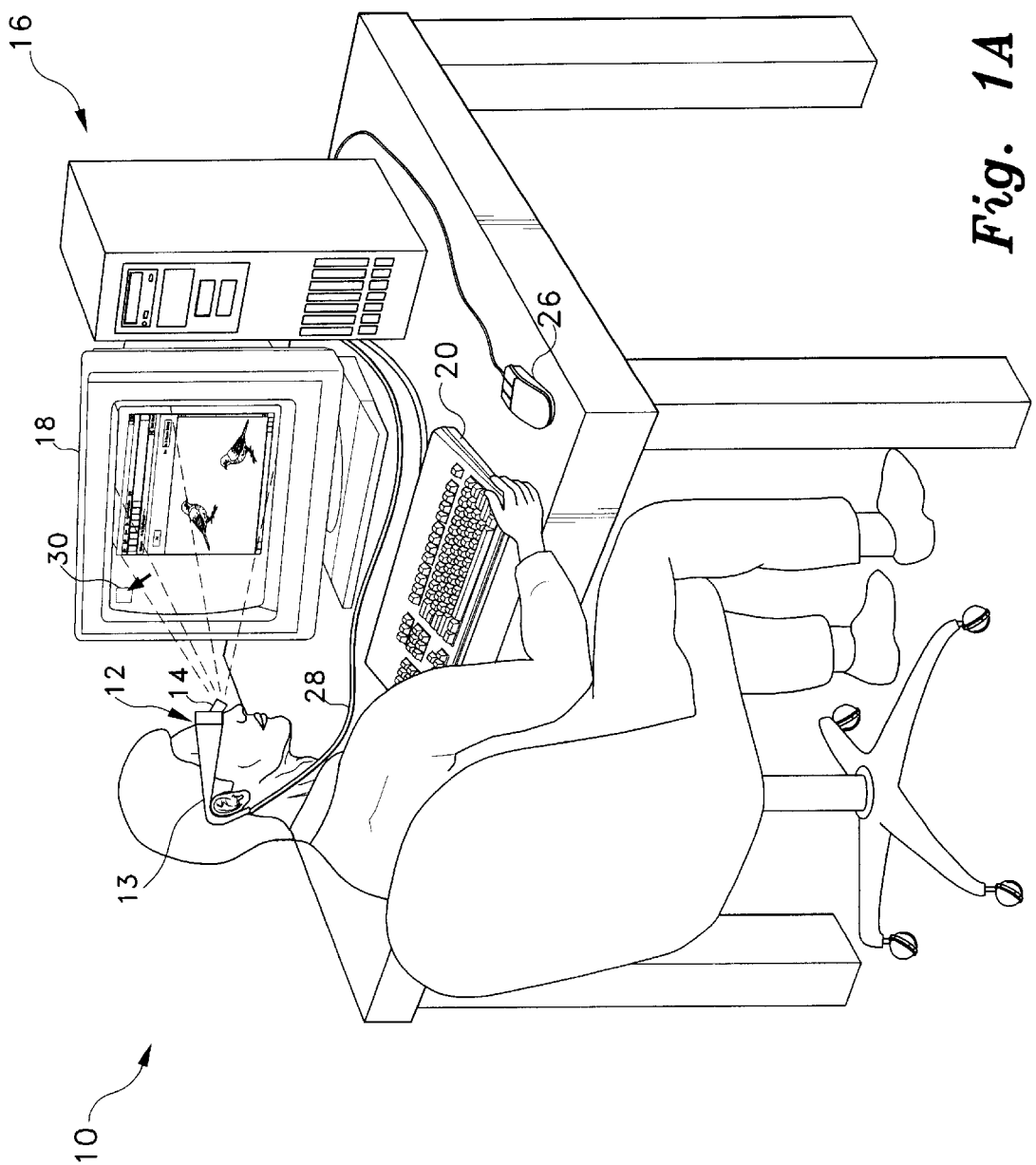
FIG. 1A is an environmental, perspective view of the gaze tracking system according to the present invention.
Figure 1B:
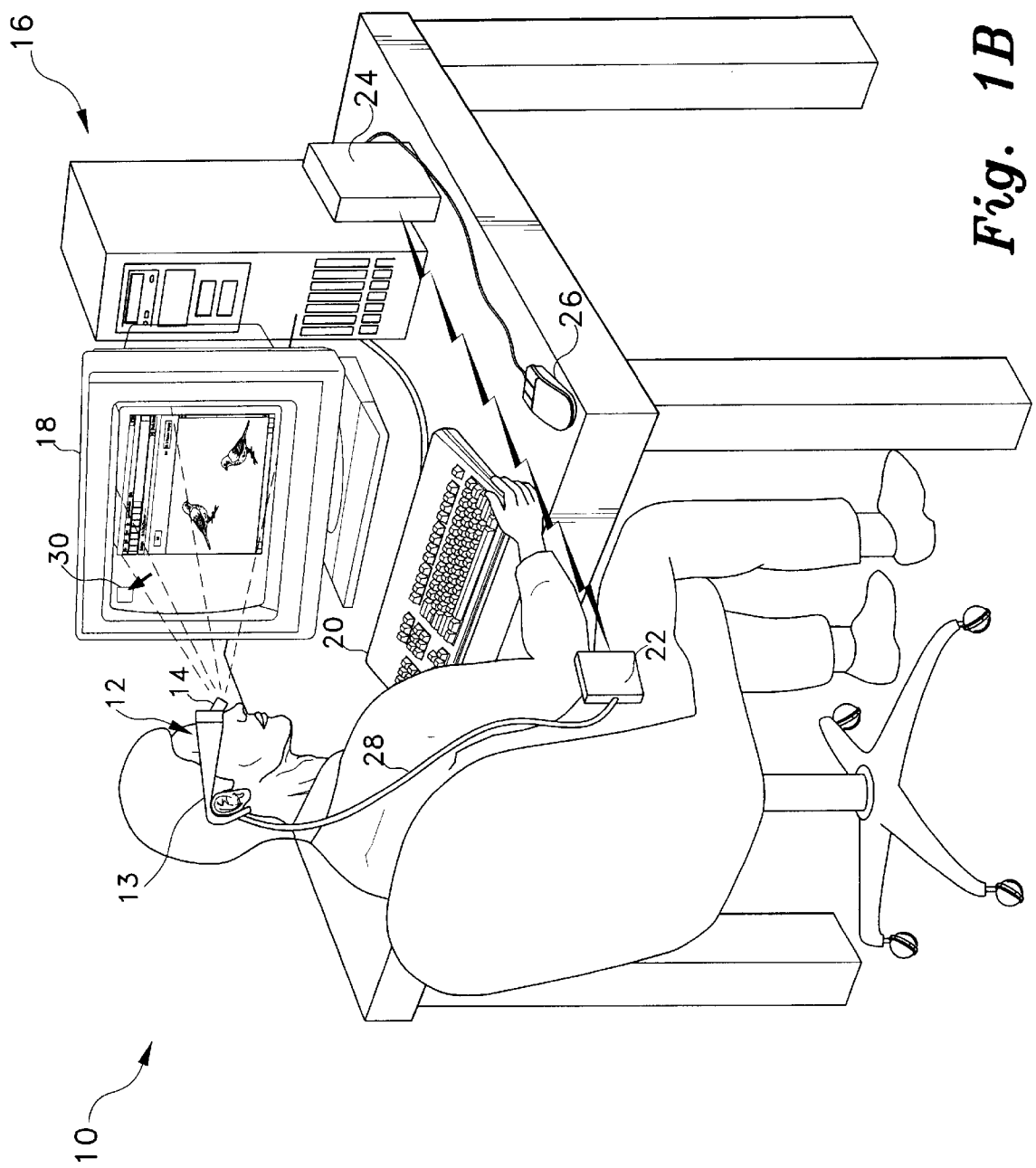
FIG. 1B is an alternative embodiment of the present invention wherein the tracking input device is in wireless communication with the computer.

As shown FIG. 1A, the eye-tracking system 10 comprises an eye-tracking input device 12 having a camera 14 mounted on a set of eyeglasses 13, substantially fixing the position of the camera 14 relative to the eye of the user. The camera may be a charge-coupled-device (CCD) or CMOS video camera, both technologies being well known to those skilled in the art. The camera is electrically coupled to a computer 16 for digitization and processing of the digitized image data. The computer 16 determines the center of the user's eye and displays a cursor 30 on the video screen 18 at the point of regard of the user's gaze. FIG. 1B illustrates another embodiment of the eye-tracking system having a wireless transmitter 22 transmitting digital data received by the camera 14 to a receiver 24 coupled to the computer 16.

As shown in the block diagram of FIG. 2, the eye-tracking system 10 has the architecture of any type of known computer having a display 18, keyboard 20, standard computer mouse 26, memory 34, CD reader 36, floppy disk drive 38, and CPU 42. The eye-tracking input device 12 and eye-tracking interface 44 operates to provide the user with an alternative for, or supplement to, the standard mouse 26. The eye-tracking interface 44 operates to digitize the analog video image of the user's eye transmitted by the camera 14 and provide input to the program instruction code, stored in computer memory 34. The eye-tracking interface may be one of several frame-grabbing products known and available to those knowledgeable in the art. The program instruction code implementing the eye-tracking algorithm is recorded onto standard computer readable medium and read into memory 34 using the CD reader 36 or floppy disk drive 38. Alternatively, the program instruction code may be read directly from another computer via the communication port 42.

Figure 3A:
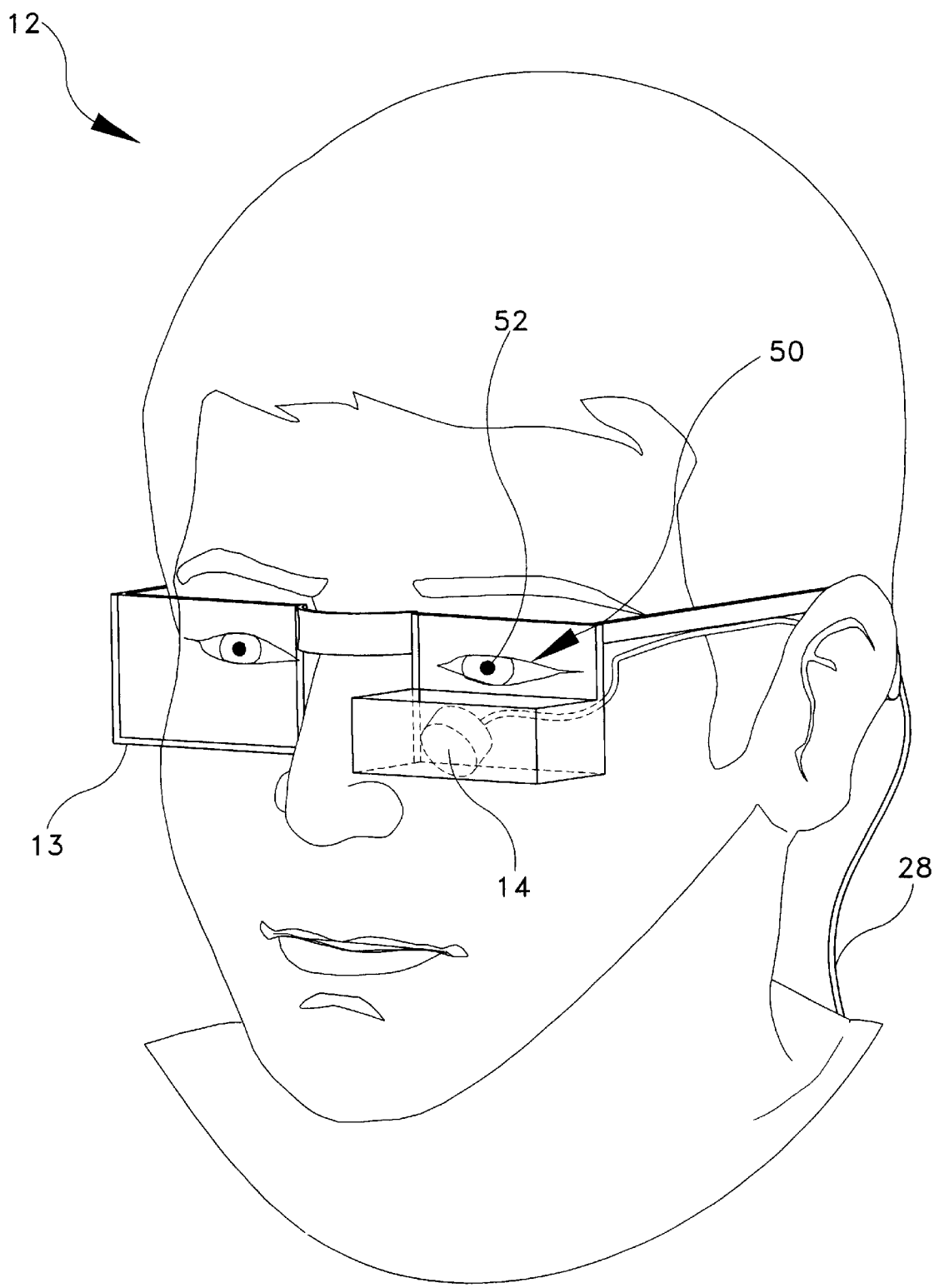
FIG. 3A is a perspective view of the camera and support means according to the present invention.

As shown in FIG. 3A, the eye-tracking input device comprises an eyeglass frame 13 or goggles with a camera 14 pointed at the user's eye 50, and a cable 28 transmitting the video image to the image digitizer.

Figure 3B:
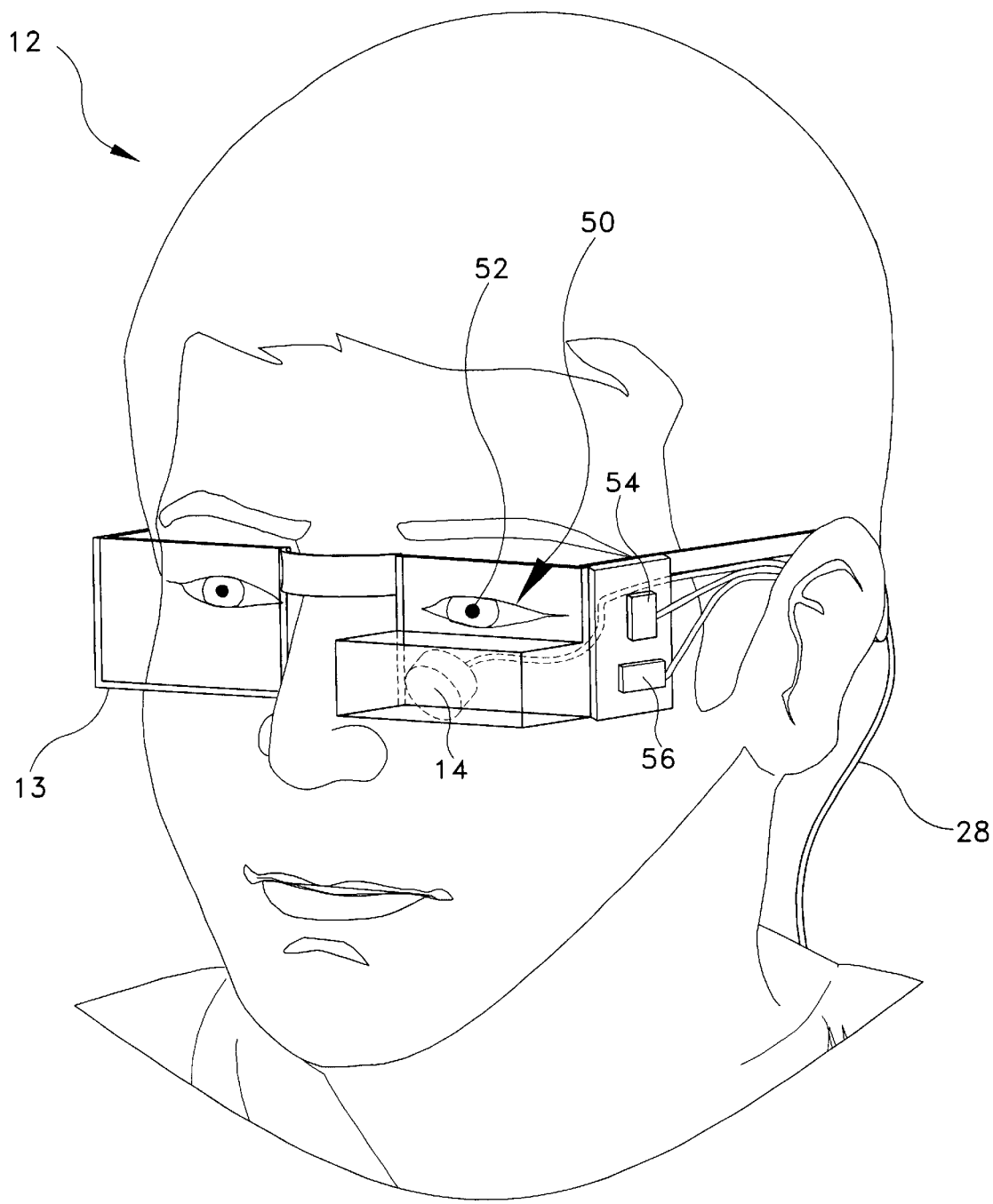
FIG. 3B is a perspective view of the camera, attitude sensors, and support means according to the present invention.

As shown in FIG. 3B, an alternative embodiment of the eye-tracking input device 12 has compass and level sensors 57, 56 for measuring axial movement of the camera. Axial position data transmitted to the computer allows for compensation due to inadvertent movement of the camera, screen, or both relative to the user's eye after startup. Miniature compass sensors which easily interface to computers are known to those skilled in the art, and includes the Model 1525 compass sensor manufactured by Dinsmore Instrument Company. The Dinsmore sensor outputs a continuous analog signal capable of being decoded to any degree of accuracy. The basic transducer is such that one revolution produces one full sine wave and cosine wave superimposed on a DC voltage such that the total output voltage is always positive on both the outputs for any position. The sine wave and cosine wave output can be processed by linear circuits and digital circuits combined together to give two square wave outputs which are 90 degree out of phase. The processing for higher resolution involves generating additional sine waves of different angles by proper combination of the two main sinusoidal signals in appropriate proportion. These sinusoidal waves are first converted to square waves and additional digital logic generates only two square waves with proper combination of these multiple square waves at different phases. A single pair of wave outputs is able to give resolution of ten micrometers. The number of pairs of square waves required may be decided as per the resolution requirement for the specific environment. The compass sensor and the level sensor use the same basic sensor, the compass sensor using a magnetic arrangement, and the level sensor using a pendulum.

Figure 3C:
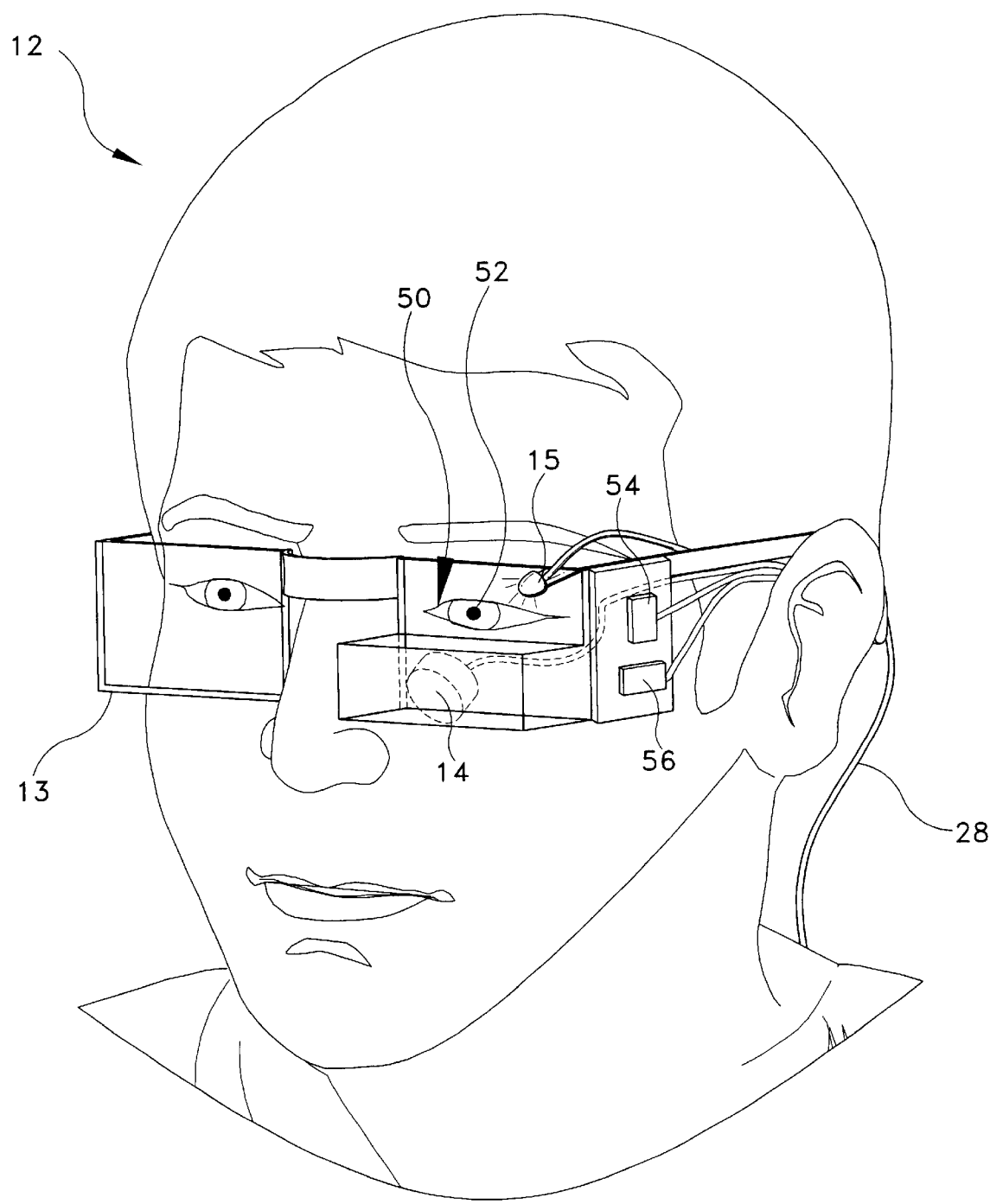
FIG. 3C is an alternative embodiment of the present invention wherein an infrared light source is mounted on the support means.

For situations where the user's eye is insufficiently illuminated to differentiate the pupil, a light source 15, shown in FIG. 3C, may be mounted on the eyeglasses to illuminate the eye. Light sources which may be used depending upon the application include incandescent lights, lighting through fiber optic cables, visible-light LEDs, and infrared-light LEDs. However, because CCD video cameras are extremely sensitive to infrared illumination, it is preferred that infrared LEDs be used as the light source. Infrared LEDs are also valuable because IR light is not visible to the user.

Figure 4:
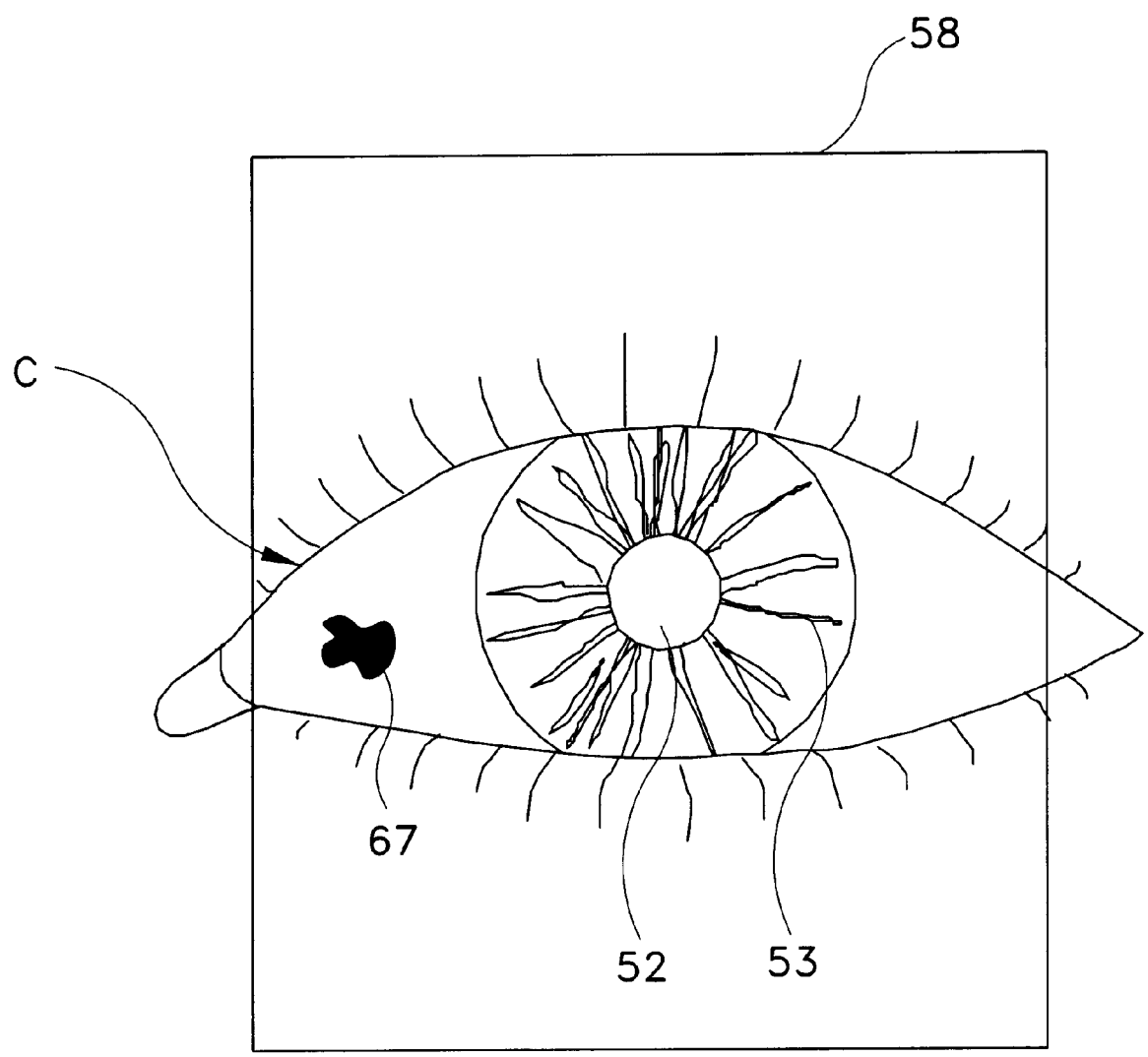
FIG. 4 is an image of the eye and the rectangular boundary of the camera image according to the present invention.
Figure 6:
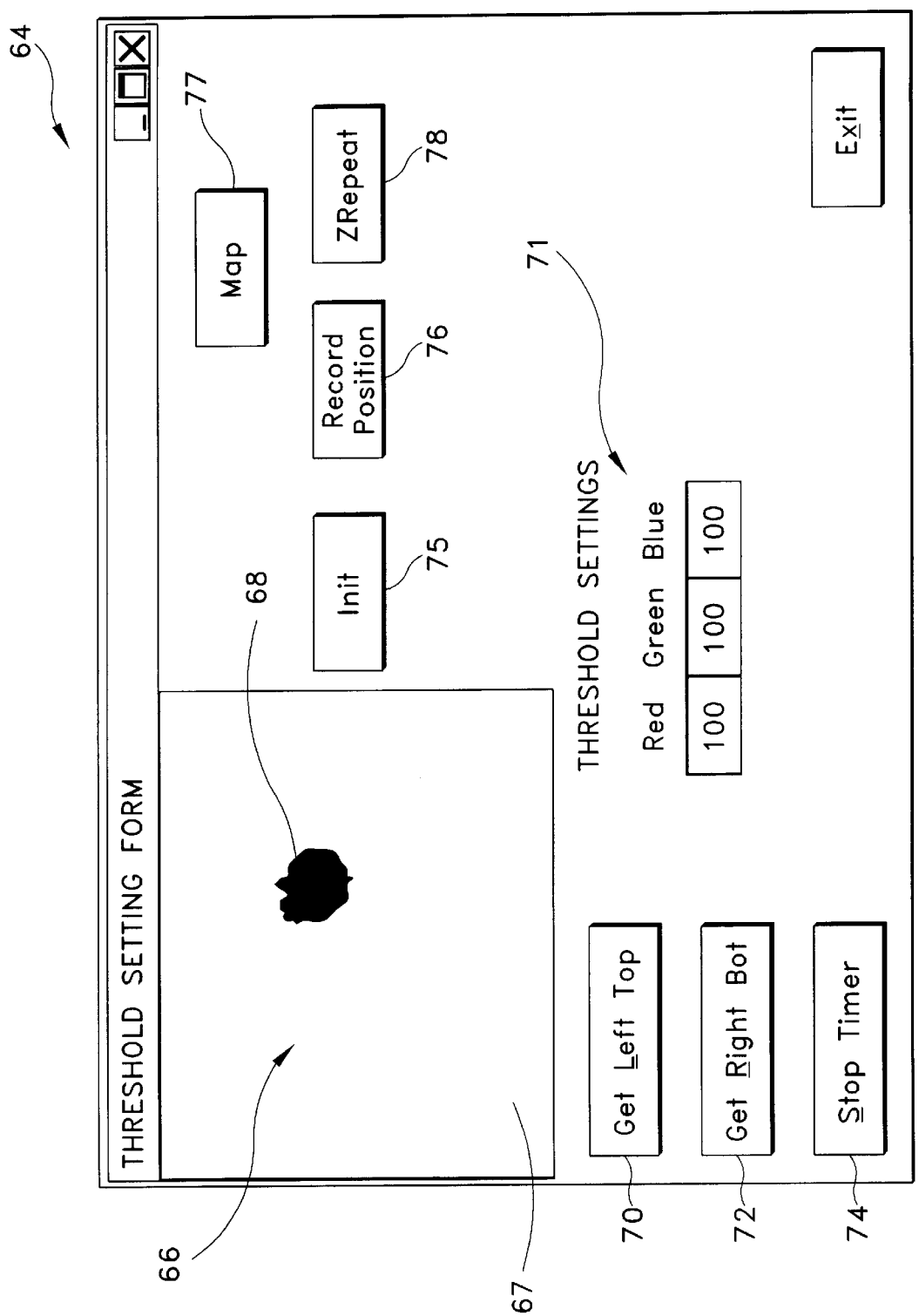
FIG. 6 is a computer display of the Threshold Setting Form having a set of RGB threshold values less than that of FIG. 5.
Figure 7:
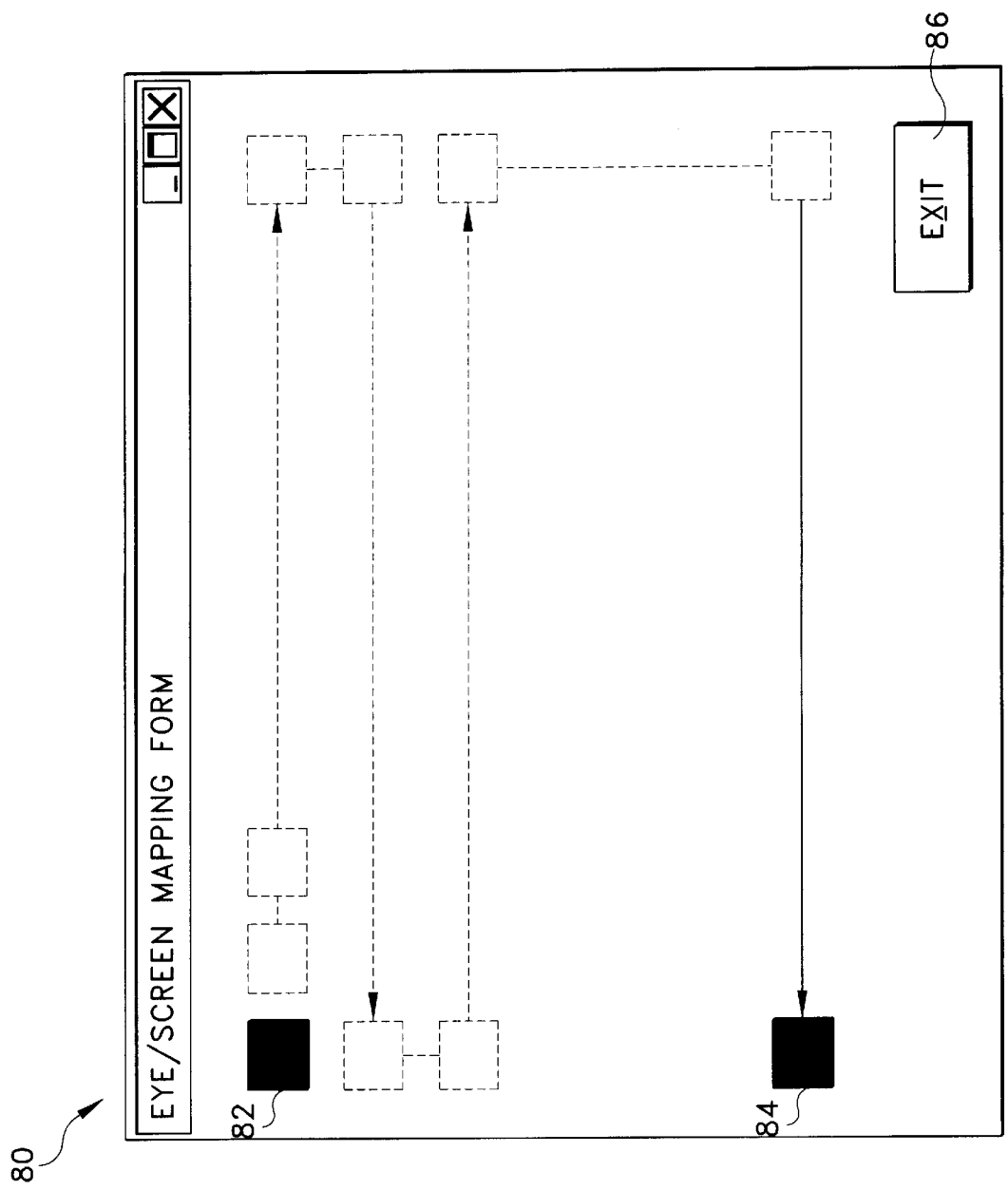
FIG. 7 is a computer display of the Eye-Screen Mapping Form according to the present invention.
Figure 8:
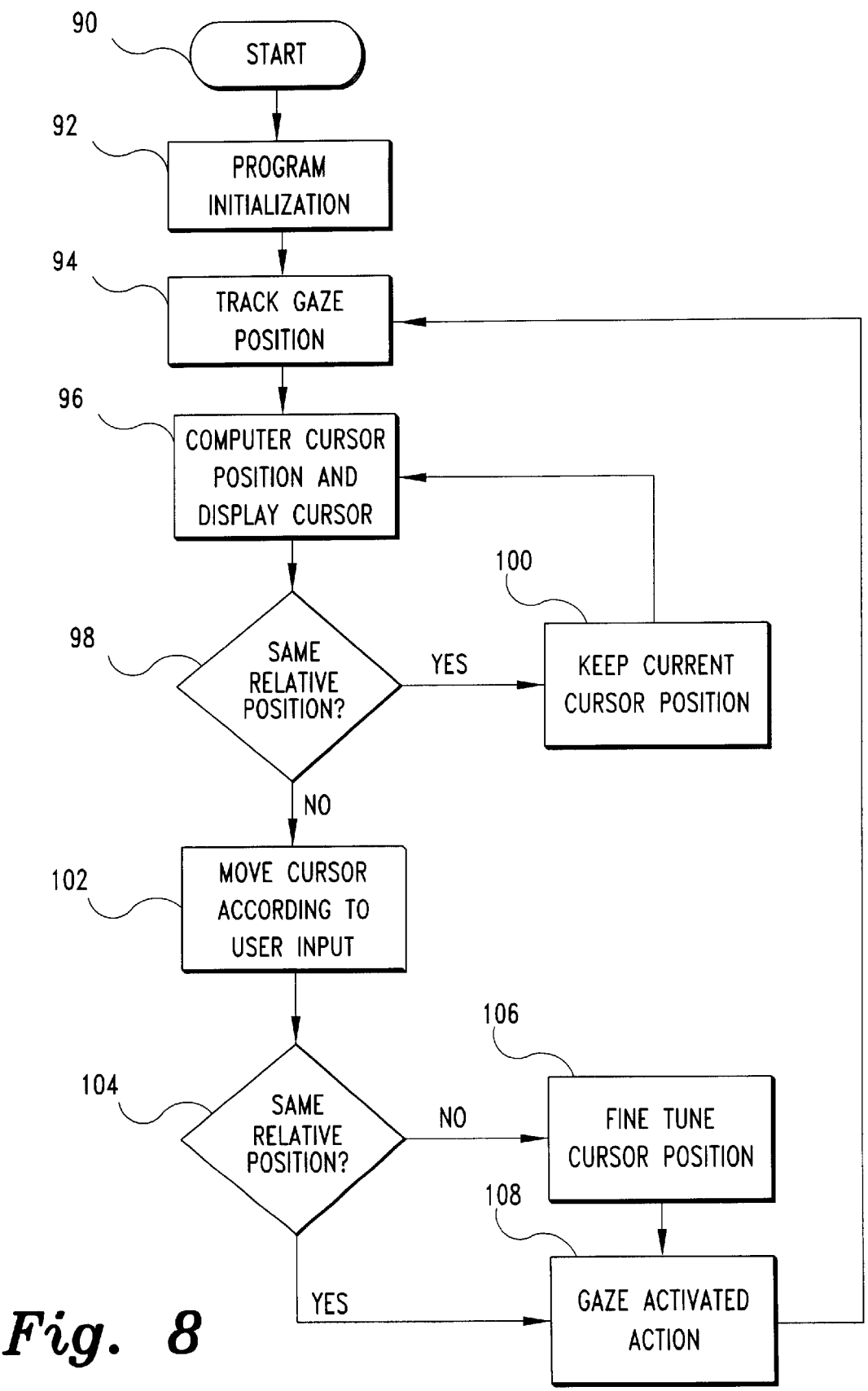
FIG. 8 is a flowchart illustrating the operation of the gaze tracking system according to the present invention.

The flowchart of FIG. 8 illustrates the high level processing performed by the eye-tracking program instruction code. Upon startup 90, the program enters an initialization phase 92, which as shown in FIGS. 4–7, interactive forms are displayed on the video screen. FIG. 4 displays a typical digital pixel image 58 of the user's eye as it appears following acquisition by camera 14 and digitization by the eye-tracking interface 44. Referring to FIG. 4, a pupil 52, an iris 53, and a shadow area 54 are visible within the eye 50.

Figure 5:
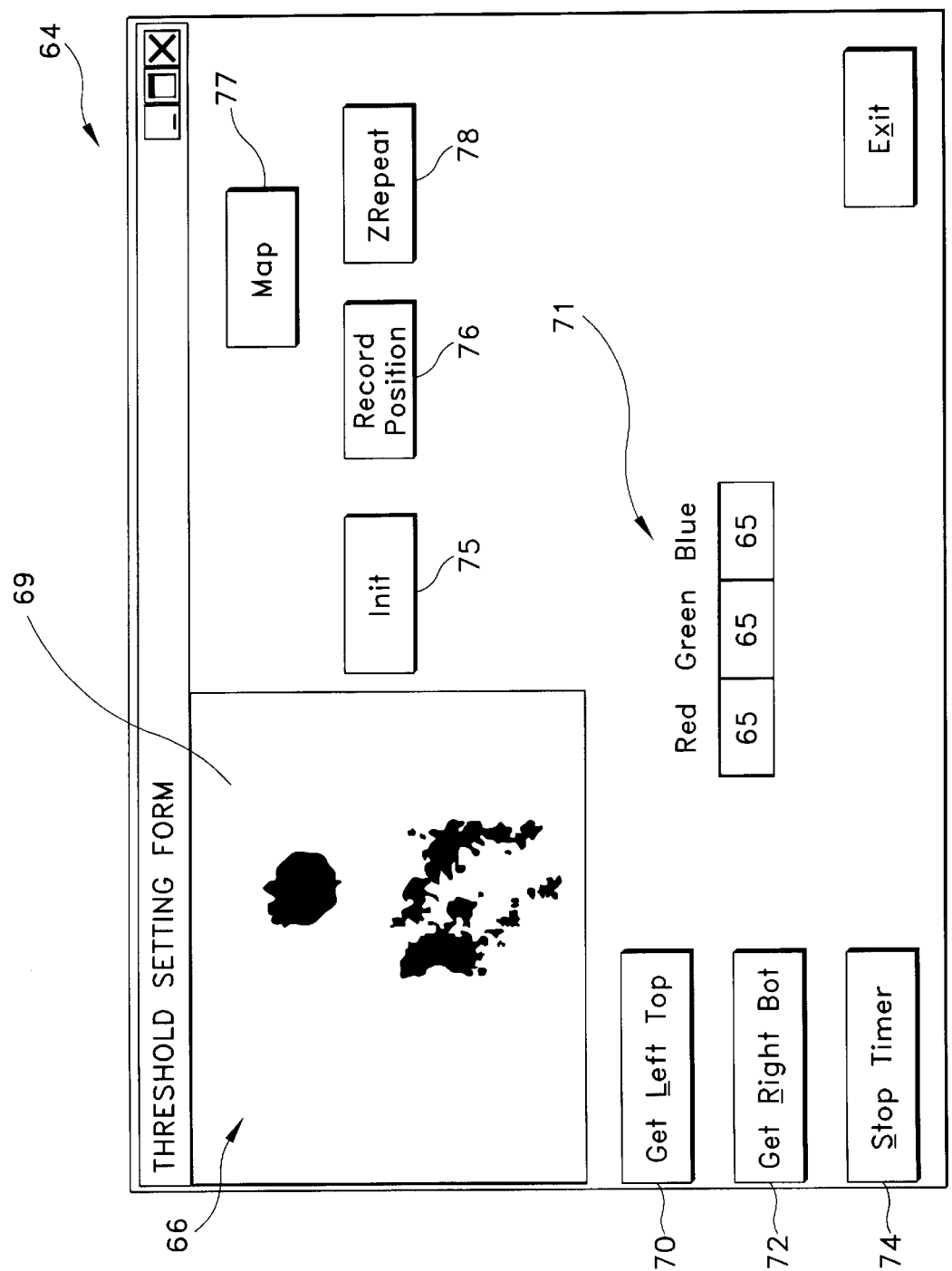
FIG. 5 is a computer display of the Threshold Setting Form having one set of RGB threshold values.

Threshold Setting Form 64, as shown in FIG. 5, provides an input means 71 for the user to select optimum RGB threshold settings which are used to generate an image in rectangular window 66, the image being the result of segmenting the digital image 58 into either a black or white pixel group. User controls 70, 72, 74, 75 and 76 select the portion of image 58 that appear in rectangular window 66. If any of the three RGB intensity levels of a pixel in image 58 is higher than the desired threshold, the corresponding pixel in window 66 is segmented into the white group. Only if all three RGB values are less than the RGB threshold levels, is the corresponding pixel in window 66 set to black. The user select the threshold for each RGB level based upon the clarity of the pupil, and as shown in FIG. 6, the RGB threshold setting of (65, 65, 65) eliminates the shadow area 67 visible in FIG. 5 captured with RBG settings (100, 100, 100), without detracting from the clarity of the pupil 68.

Once the user has selected the optimum RGB threshold settings, the center of the pupil is mapped into a display screen coordinate space for substantially the entire display screen area. This mapping data is written to a file and stored in memory 34. The file can be stored in different formats or in different computers, however, in the present invention, the file is stored a text file having a multiplicity of lines, each line having two pairs of coordinates, the first pair denoting the logical position of the center of the pupil as determined by the digital representation of the eye image, and the second pair denoting the coordinates of a moving cursor upon which the user is gazing. The mapping data is generated using the Eye-Screen Mapping Form 80 as shown in FIG. 7. A cursor starts at an initial position 82 and ends at a final position 84, moving in such a way as to traverse the entire video screen, the cursor remaining in any one position approximately 200 milliseconds. At each position on the screen, the program determines the coordinates of the center of the pupil within the image coordinate space defined by the digital representation of the pixel image of the eye as determined by the RGB threshold settings. Based upon a user selected digital eye image of 200 pixels by 200 pixels, the program processes an array of 200 by 200, each position having a "1" or a "0" corresponding to a black group or a white group. Starting from left to right, the program determines the left most border of the pupil by detecting the first appearance of three black sections in a row. The program performs this analysis for the left, right, top and bottom perimeters the pupil and based upon these values, determines the coordinates of the center of the pupil by simply finding the middle of the rectangle thus formed. An initialization file thus formed has as many rows as screen coordinates mapped.

Upon selection of the "ZRepeat" 78 control, the program exits the initialization phase 92 as shown in FIG. 8 and enters the gaze tracking phase 94 which runs in background mode on the CPU 32, computing new eye positions every five times a seconds. Tracking frequency could be faster or slower, the present invention selecting five times a second as an optimum value based upon experimentation. The program instruction code keeps track of the last three positions of the center of the pupil. After each sampling, the new position is compared to the last three positions and if it is more than a certain threshold value in any direction, the pointer is positioned accordingly 96–102.

At any time, or if the position of the pointer does not overlap the point of regard 104, the user can enter fine tuning mode 106 by locking their gaze for a predetermined length of time, presently set to one second, and then quickly glancing at the extreme position to which the user wishes the pointer to move. At this point the software moves the pointer in small increments every 40 milliseconds in the direction required. At the same time, the program displays a popup menu 114, as illustrated in FIG. 9, at a location on the display opposite to the point of regard. The user then locks their gaze upon the action button desired, moving the pointer 112 to the new point of regard, still remembering the previous point of regard which the user wishes to "click". Once the pointer 112 overlaps the intended action to select, the user selects the action as a result of gazing at the action area or by blinking 108. Blinking of the user's eyes is easily identified as the density of "dark" segments diminishes significantly in the area of the eye. Selection of an action 108 could also be accomplished by other means such as pressing the "Enter" key on a keyboard or by a speech recognition program configured to respond to voice commands. The pointer 112 may be programmed to form a "crosshair" or other visual indicator in fine-tuning mode providing a more responsive man-machine interface. Fine tuning mode 106 may be canceled at any given moment by various combinations of blinking, gazing or a separate button on the menu. In addition, fine tuning mode 106 is meant for fine adjustments only and will be canceled if the desired movement exceeds a predetermined distance or period of inaction.

It is to be understood that the present invention is not limited to the embodiments described above, but encompasses any and all embodiments within the scope of the following claims.

We claim:

1. An eye-tracking system for tracking the point of regard of a user's gaze comprising:

camera means for acquiring a video image of the user's eye;

support means, connected to the camera means, for fixing the relative physical positions of the camera means;

video digitizing means, connected to the camera means, for accepting the video image of the user's eye and converting the video image to a digital image;

computer means electrically connected to the video digitizing means, further comprising a central processing unit, a memory, a video display screen, eye-tracking interface, and computer readable program code means stored in the memory, wherein the code means further comprising:

first instruction means for determining the center of the user's eye within the digital image;

second instruction means for correlating the determined center of the user's eye to a point of regard on the display screen;

third instruction means for accepting the correlated data and placing a display screen pointer at a position on the display screen substantially overlapping the point of regard; and fourth instruction means for providing the user with a display screen menu activated by eye movement;

fifth instruction means for selecting RGB pixel intensity threshold values for the digital image;

sixth instruction means for segregating the digital pixel data into two separate binary groups as first and second groups using the RGB threshold values as a discriminator; and seventh instruction means for substantially determining the position of the center of the eye in accordance with the segregated pixel data and the axial position of the support means;

whereby the eye-tracking system positions a pointer on the video screen at the point of regard of the user's gaze and provides the user with an eye movement activated method for selecting computer-programmable activities.

2. The system of claim 1, wherein the code means further comprises:

eighth instruction means for storing to memory a map correlating a substantial portion of a display screen coordinate space to a pre-determined position of the center of the user's eye, thereby facilitating the positioning of the display screen pointer;

ninth instruction means for using eye movement to fine-tune the position of the display screen pointer; and tenth instruction means for performing user defined actions based upon the length of time a user has locked their gaze upon a point of regard.

3. The system of claim 1, wherein the support means substantially fixes the position of the user's eye relative to the camera.

4. The system of claim 1, further comprising a light source disposed on the support means, whereby the center of the user's is illuminated.

5. An eye-tracking system for tracking the point of regard of a user's gaze comprising:

camera means for acquiring a video image of the user's eye;

support means, connected to the camera means, for fixing the relative physical positions of the camera means;

compass and level sensing means for acquiring axial position data for the support means;

video digitizing means, connected to the camera means, for a accepting the video image of the user's eye and converting the video image to a digital image;

computer means electrically connected to the video digitizing means and attitude sensor means, further comprising a central processing unit, eye-tracking interface, a memory, a video display screen, and computer readable program code means stored in the memory, wherein the code means further comprising:

first instruction means for determining the center of the user's eye within the digital image;

second instruction means for correlating the determined center of the user's eye and the axial position of the attitude sensors to a point of regard on the display screen;

third instruction means for accepting the correlated data and placing a display screen pointer at a position on the display screen substantially overlapping the point of regard; and fourth instruction means for providing the user with a display screen menu activated by eye movement;

whereby the eye-tracking system positions a pointer on the video screen at a point of regard of the user's gaze, and provides the user with an eye movement activated method for selecting actions relative to the point of regard.

6. A computer useable medium having computer readable program code means embodied thereon, the computer readable program code means comprising:

first instruction means for selecting an image coordinate space of the eye;

second instruction means for determining RGB threshold values in accordance with a user selected representation of the digital pixel data corresponding to the selected image space;

third instruction means for segregating the digital pixel data into two separate binary groups as first and second groups using the RGB threshold values as a discriminator; and fourth instruction means for determining the logical position of the center of the eye within the image space in accordance with the segregated data.

7. The computer medium of claim 6, wherein the code means further comprises:

fifth instruction means for processing horizontal and vertical position data relative to the source of the image coordinate space of the eye;

sixth instruction means for mapping the logical position of the center of the user's eye from the image space into a position within a coordinate space of the video display;

seventh instruction means for accepting data corresponding to the determined position of the center of the eye and placing a cursor at the pre-determined position on the display screen;

eighth instruction means for fine-tuning the position of the cursor on the display screen; the instruction means to determine the length of time a user locks their gaze upon a point of regard; and tenth instruction means for performing user defined actions based upon the length of time a user locks their gaze upon a point of regard.

* * * * *